(12) United States Patent
Chen et al.

(10) Patent No.: US 8,440,423 B2
(45) Date of Patent: May 14, 2013

(54) BIOREMEDIATION OF NANOMATERIALS

(75) Inventors: Frank Fanqing Chen, Moraga, CA (US); Jay D. Keasling, Berkeley, CA (US); Yinjie J. Tang, St Louis, MO (US)

(73) Assignee: U.S. Department of Energy, Washington, DC (US)

( * ) Notice: Subject to any disclaimer, the term of this patent is extended or adjusted under 35 U.S.C. 154(b) by 305 days.

(21) Appl. No.: 12/525,875

(22) PCT Filed: Feb. 5, 2008

(86) PCT No.: PCT/US2008/053103
§ 371 (c)(1),
(2), (4) Date: Nov. 4, 2010

(87) PCT Pub. No.: WO2008/115627
PCT Pub. Date: Sep. 25, 2008

(65) Prior Publication Data
US 2011/0039291 A1    Feb. 17, 2011

Related U.S. Application Data

(60) Provisional application No. 60/899,797, filed on Feb. 5, 2007.

(51) Int. Cl.
*C12Q 1/02* (2006.01)
(52) U.S. Cl.
USPC ............................................ 435/29; 977/773
(58) Field of Classification Search ...... 435/29; 977/773
See application file for complete search history.

(56) References Cited

U.S. PATENT DOCUMENTS 5,569,596 A * 10/1996 Caccavo et al. ............... 435/168

OTHER PUBLICATIONS

Purdue University News. 2004. Purdue researchers tackle environmental fate of nanoparticles, Purdue University News, Aug. 26, 2004, pp. 1-4. Printed Mar. 29, 2012.*
Tang et al. 2007 Charge-Associated Effects of Fullerene Derivatives on Microbial Structural Integrity and Central Metabolism. Nano Letters, vol. 7, No. 3, pp. 754-760.*
Venkateswaran et al. 1999. Polyphasic taxonomy of the genus *Shewanella* and description of *Shewanella oneidensis* sp. nov. International Journal of Systematic Bacteriology, vol. 49, pp. 705-724.*
Gorby et al. (2006. Electrically conductive bacterial nanowires produced by *Shewanella oneidensis* strain MR-1 and other microorganisms. Proceedings of the National Academy of Sciences of the United States of America, vol. 103, No. 30, pp. 11358-11363.*

* cited by examiner

*Primary Examiner* — Jon P Weber
*Assistant Examiner* — Kailash C Srivastava
(74) *Attorney, Agent, or Firm* — Mark C. Lang; Brian J. Lally; John T. Lucas

(57) ABSTRACT

The present invention provides a method comprising the use of microorganisms for nanotoxicity study and bioremediation. In some embodiment, the microorganisms are bacterial organisms such as Gram negative bacteria, which are used as model organisms to study the nanotoxicity of the fullerene compounds: *E. coli* W3110, a human related enterobacterium and *Shewanella oneidensis* MR-1, an environmentally important bacterium with versatile metabolism.

12 Claims, 7 Drawing Sheets

BIOREMEDIATION OF NANOMATERIALS

CROSS-REFERENCE TO RELATED APPLICATIONS

This application is a national stage entry of and claims priority to, PCT/US2008/053103 filed Feb. 5, 2008. This application also claims priority to provisional application 60/899,797 filed Feb. 5, 2007.

STATEMENT OF GOVERNMENTAL SUPPORT

This invention was made during work supported by the U.S. Department of Energy, Office of Science, Office of Biological and Environmental Research, and Genomics:GTL Program through contract DE-AC02-05CH11231 between the Lawrence Berkeley National Laboratory and the US Department of Energy. This work was also supported by NIH grant R21CA95393-01 (F.F.C.), by DOD grant BC045345 (F.F.C.), and by DARPA grant F1ATA05252M001 (F.F.C.). The government has certain rights in this invention.

FIELD OF THE INVENTION

The present invention relates to bioremediation of carbon-based nanoparticles and nanomaterials using microorganisms. The present invention also relates to conducting metabolic pathway studies using isotopomer analysis.

BACKGROUND OF THE INVENTION

Nanotechnology is being applied to a diverse array of products, ranging from cosmetics, printer toners, clothing, electronics, and even drug delivery vehicles. Carbon nano-materials, such as fullerenes and nanotubes, have been the most extensively used nanoparticles due to their unique and superior physical and chemical properties, including large surface areas, high electrical conductivity, and excellent mechanical strength. Fullerenes, also called $C_{60}$ or buckyballs, and other fullerene derivatives, are the most well studied and most commonly used carbon nanomaterials. Recently, fullerenes were investigated as potential microbicides; other potential in vivo applications were explored as well. However, the toxicological definition for fullerene is still quite controversial. Early studies have indicated that a repeating subchronic topical dose of fullerenes on mouse skin for up to 24 weeks is non-carcinogenic (Nelson, M. A.; Domann, F. E.; Bowden, G. T.; Hooser, S. B.; Fernando, Q.; Carter, D. E. *Toxicol Ind Health* 1993, 9, (4), 623-30). The Ames assay also indicates that the fullerene is not mutagenic and of no toxicological significance (Mori, T.; Takada, H.; Ito, S.; Matsubayashi, K.; Miwa, N.; Sawaguchi, T. *Toxicology* 2006, 225, (1), 48-54). Yet, recently, fullerenes have been suggested to be carcinotoxic and genotoxic, although only upon photosensitization. In addition, $C_{60}$ derivatives have demonstrated superoxide dismutase mimetic properties; they can also generate free radicals, can be photosensitized, and mutagenic. In contrast, others indicate that fullerenes have avid reactivity with free oxidative radicals, acting as radical scavengers and antioxidants instead.

In general, water-soluble fullerenes are cytotoxic, which can be attenuated by surface derivatization (Sayes, C. M.; Fortner, J. D.; Guo, W.; Lyon, D.; Boyd, A. M.; Ausman, K. D.; Tao, Y. J.; Sitharaman, B.; Wilson, L. J.; Hughes, J. B.; West, J. L.; Colvin, V. L. *Nano Letters* 2004, 4, (10), 1881-1887). However, a recent report demonstrated the opposite results (Chiron, J.; Lamande, J.; Moussa, F.; Trivin, F.; Ceolin, R. *Ann Pharm Fr.* 2000, 58, (3), 170-175). Isakovic et al, in *Biomaterials* 2006, 27, (29), 5049-58, suggested that the trace amount of THF in the fullerene toxicity studies was responsible for the cytotoxicity. It has also been shown that cationic fullerenes are moderately toxic (Bosi, S.; Da Ros, T.; Castellano, S.; Banfi, E.; Prato, M. *Bioorg Med Chem Lett* 2000, 10, (10), 1043-5) and it has been suggested that these fullerenes affect energy metabolism. Mashino, T.; Nishikawa, D.; Takahashi, K.; Usui, N.; Yamori, T.; Seki, M.; Endo, T.; Mochizuki, M. *Bioorg Med Chem Lett* 2003, 13, (24), 4395-7. In contrast, anionic fullerenes have been shown to be relatively less toxic by some reports, yet other reports indicate that anionic fullerenes can inhibit bacterial growth, (Tsao, N.; Luh, T. Y.; Chou, C. K.; Wu, J. J.; Lin, Y. S.; Lei, H. Y. *Antimicrob Agents Chemother* 2001, 45, (6), 1788-93) more specifically that anionic fullerene derivatives (carboxyfullerene) affect Gram positive bacteria (such as *Streptococcus pyogenes*), but have no affect on Gram negative bacteria (such as *Escherichia coli*) at concentrations up to 500 mg/L. (Tsao, N.; Luh, T. Y.; Chou, C. K.; Chang, T. Y.; Wu, J. J.; Liu, C. C.; Lei, H. Y. *J Antimicrob Chemother* 2002, 49, (4), 641-9). The strong cytotoxicity of cationic fullerene compounds (e.g., ammonium or other amino acid-derivatized fullerene) has been shown in many microorganisms. It has also been shown that the presence of light-induced reactive oxygen species (ROS) enhance fullerene anti-microbial activity. The current hypothesized nanotoxicity mechanisms include suppression of energy metabolism (e.g. TCA cycle), oxidative damage to crucial proteins and enzymes, and increased membrane permeability, causing its rupture. (Jensen, A.; Wilson, S.; Schuster, D. *Bioorg Med Chem Lett* 1996, 9, (20), 2959-62; Sayes, C.; Gobin, A.; Ausman, K.; Mendez, J.; West, J.; Colvin, V. *Biomaterials* 2005, 26, (36), 7587-95). Since mechanisms of cytotoxicity obtained from animal/human cell models may not be compatible with microbial models, the exact molecular mechanisms for the inhibition of bacterial growth are still not fully understood. Furthermore, the majority of nanoparticle antibacterial experiments were not performed at the molecular and metabolic levels, which are central for bacterial survival and proliferation.

BRIEF SUMMARY OF THE INVENTION

The present invention provides a method comprising the use of organisms for nanotoxicity study and bioremediation. In one embodiment, the organisms are bacteria. In a preferred embodiment, the bacterial organisms are Gram negative bacteria used as model organisms to study the nanotoxicity of the fullerene compounds: *E. coli* W3110, a human related enterobacterium and *Shewanella oneidensis* MR-1, an environmentally important bacterium with versatile metabolism.

The present invention provides for a method for bioremediation of nanomaterials from a liquid mixture, comprising: (a) providing a solution containing nanomaterials in suspension; (b) adding a sufficient amount of a microorganism to said solution; (c) providing a sufficient period of time for the microorganism to aggregate the nanomaterials and precipitate the nanomaterials; and (d) separating the precipitated nanomaterial and the remaining solution.

The present invention provides for a method for bioremediation of nanomaterials from a liquid mixture, comprising the steps of (a) providing a sample solution containing nanomaterials in suspension; (b) adding a sufficient amount of *Shewanella* cell culture to said sample solution; (c) waiting a sufficient period of time to allow the cells to aggregate the nanomaterials and precipitate; (d) removing the remaining supernatant of the sample solution.

In one aspect, the invention provides a method for bioremediation of nanomaterials and other nanoparticles (e.g., metal, metal oxides, semiconductors). In one embodiment, the invention provides for the cleanup of fullerene compounds from a liquid mixture, which should prove to be a cost-effective method of clean-up for fullerene manufacturers.

The present invention further provides for a method of reducing or preventing biofouling in a bioremediation system, comprising the use of a nanomaterial, such as a fullerene or derivative thereof, to inhibit the growth of a microorganism involved in the bioremediation system. The nanomaterial can be added to any medium containing the microorganism such that the nanomaterial contacts a microorganism resulting in the inhibition of the growth of the bacterium.

The present invention also provides for a method for indexing toxicity of nanomaterials comprising comparing isotopomer data with standards to detect the change of certain enzymatic reactions in cell metabolism under various environmental and genetic stresses with aid of powerful isotopomer measurement tools (such as CE-MS or FT-ICR).

The present invention also provides for a method of [3-$^{13}$C] isotopomer analysis of metabolites (e.g. amino acids) for indexing the toxicity of carbon-based nanomaterials at the metabolism level to mechanistically study the cellular and biomolecular machineries affected by nanomaterials, to determine the effect of nanoparticles on central carbon and energy metabolism, and the effect of perturbation of central metabolism of cells treated with carbon-based nanomaterials and compounds.

The present invention also provides for a method for indexing toxicity of a nanomaterial on a cell, comprising: (a) providing a cell culture; (b) culturing the cell culture in a growth medium comprising a plurality of labeled carbon substrate isotopomers; (c) adding a nanomaterial to the growth medium; and (d) determining the labeling pattern of the cellular metabolites of the cells in the cell culture.

In one aspect, the present invention provides a method of metabolic isotopomer analysis for indexing the toxicity of carbon-based nanomaterials at the metabolism level. The present method can be used to mechanistically study the cellular and biomolecular machineries affected by nanomaterials, to determine the effect of nanoparticles on central carbon and energy metabolism, and the effect of perturbation on certain metabolic reactions of cells treated with carbon-based nanomaterials and compounds (FIG. 1).

In some embodiments, bacteria is grown on [$^{13}$C]-lactate thereby allowing the measurement of the isotopomer distribution in metabolites (often amino acids) from nanoparticle exposed cell populations to give insight into whether the toxicity of nanomaterials affects an organism's entire metabolome (change of the metabolic pathway or fluxes). In one embodiment, the [$^{13}$C]-lactate is [3-$^{13}$C]L-lactate.

In another embodiment, that method also comprises comparing isotopomer data with standards to detect the change of certain enzymatic reactions in cell metabolism under various environmental and genetic stresses. Potentially, the isotopic labeling is a high throughput approach complementary to microarray study (while using isotopic abundance in metabolites instead of gene expression level) to figure out the change of in vivo enzymatic reaction activities with aid of powerful isotopomer measurement tools (such as CE-MS or FT-ICR).

BRIEF DESCRIPTION OF THE DRAWINGS

The foregoing aspects and others will be readily appreciated by the skilled artisan from the following description of illustrative embodiments when read in conjunction with the accompanying drawings.

FIG. 6. a) Isotopomer distribution in proteogenic amino acids of *S. oneidensis* MR-1 cultured in [3-$^{13}$C] L-lactate medium. The GC-MS data include 14 amino acids ((M57)+ and (M159)+ mass values) for all three nanoparticle-stressed experiments (○ 80 mg/L $C_{60}$—OH; □ 80 mg/L $C_{60}$—COOH; ♦ 20 mg/L $C_{60}$—NH$_2$), which indicates the central metabolism pathways for producing small molecules are not altered by presence of nanoparticles. The dotted lines represented absolute variances (+0.05) of measured GC-MS data based on batch cultures. b) Isotopomer distribution in proteogenic amino acids of ten *S. oneidensis* MR-1 mutants cultured in

[3-13C] L-lactate medium. Nine mutants give the same isotopomer data as the control, which indicates the mutagenesis dose not affect the central metabolism of those mutants. The outliers ◇ and ☐ are histidine and serine GC-MS data from SO0781 (deficiency in glycine→C1 pathway) shows the 5, 10-Me-THF synthesis pathways are altered.

Figure 7:
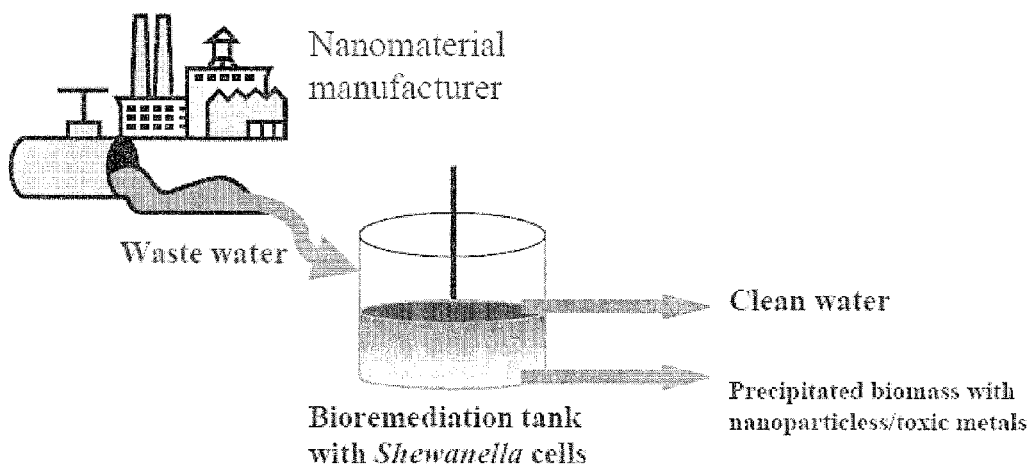

FIG. 7. Cartoon drawing showing the method used to treat waste water having been contaminated with nanomaterials.

Figure 8:
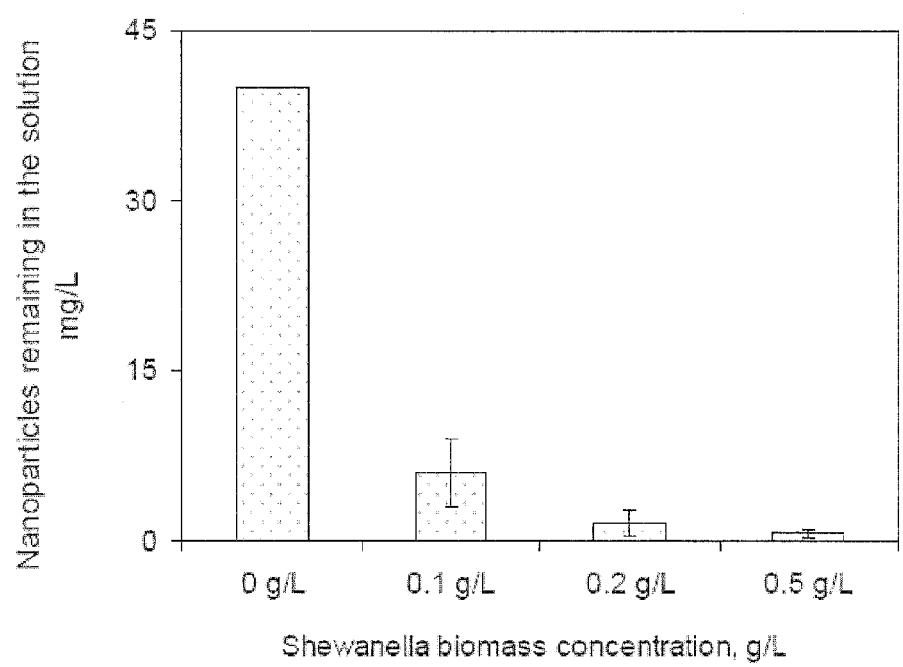

FIG. 8. Graph showing that as the amount of cell culture increases, the concentration of nanoparticles in solution decreases.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nanoparticle" includes a plurality of nanoparticles, and so forth.

These and other objects, advantages, and features of the invention will become apparent to those persons skilled in the art upon reading the details of the invention as more fully described below.

Nanotechnology is becoming widely used, and nanomaterial toxicity has been identified. With this explosion in applications, it is important to address concerns, either legitimate or exaggerated, about the potential toxic effects of nanoparticles in both the environment, and for medical applications. There has been concern in communities over possible effects of nanomaterials on the environment. Nanomaterials may pass through filters due to their small size and also stay suspended in solution longer, also affecting any decontamination process. Concerns over chemical cleanup present other issues of safety and toxicity. The present invention describes a method whereby liquids contaminated by toxic nanomaterials can be cleaned by microorganisms, thus bringing bioremediation to a new field. By providing a method for biological cleanup, concerns over chemical contamination of precious resources can be addressed.

The present invention provides for a method for bioremediation of nanomaterials from a liquid mixture, comprising: (a) providing a solution containing nanomaterials in suspension; (b) adding a sufficient amount of a bacterial cell to said solution; (c) providing a sufficient period of time for the bacterial cell to aggregate the nanomaterials and precipitate the nanomaterials; and (d) separating the precipitated nanomaterial and the remaining solution.

In some embodiments, the nanomaterials are nanoparticles. In some embodiments, the nanoparticles are fullerene particles, metal oxides, metal, semiconductor, inorganic oxides (such as silicon oxide), and the like. In some embodiments, the nanomaterials have a size from about 1 nm to about 500 nm. A fullerene particle includes fullerene and derivatives thereof. The fullerene particles can comprise neutral fullerene compounds, negatively-charged fullerene compounds, positively-charged fullerene compounds, or a mixture thereof. The neutral fullerene compound can be $C_{60}$ or $C_{60}$—OH. The negatively-charged fullerene compound can be $C_{60}$—COOH. The positively-charged fullerene compound can be $C_{60}$—$NH_2$.

In some embodiments, the microorganism is a bacterial cell. The microorganism can be in cell culture, immobilized on a surface or substrate, on or in a membrane, manifold, porous material, biofilm, or the like. The microorganism can be a bacterium or bacterial cell. The bacterium can be any suitable environmental bacteria. The bacterium can be of the genus *Shewanella*. The *Shewanella* cell can be a cell selected from the group consisting of *Shewanella oneidensis, Shewanella putrefaciens, Shewanella baltica, Shewanella denitrificans, Shewanella frigidimarina*, or *Shewanella amazonesis*. The *Shewanella oneidensis* cell can be of the strain *Shewanella oneidensis* MR-1.

The present invention also provides for a method for indexing toxicity of a nanomaterial on a cell, comprising: (a) providing a cell culture; (b) culturing the cell culture in a growth medium comprising a plurality of labeled carbon substrate isotopomers; (c) adding a nanomaterial to the growth medium; and (d) determining the labeling pattern of the cellular metabolites of the cells in the cell culture. In some embodiments, the carbon substrate is a sole carbon source for the cell culture. In some embodiments, the determining step comprises measuring the levels of cellular metabolites with a GS-MS, CE-MS or FT-ICR.

Figure 2:
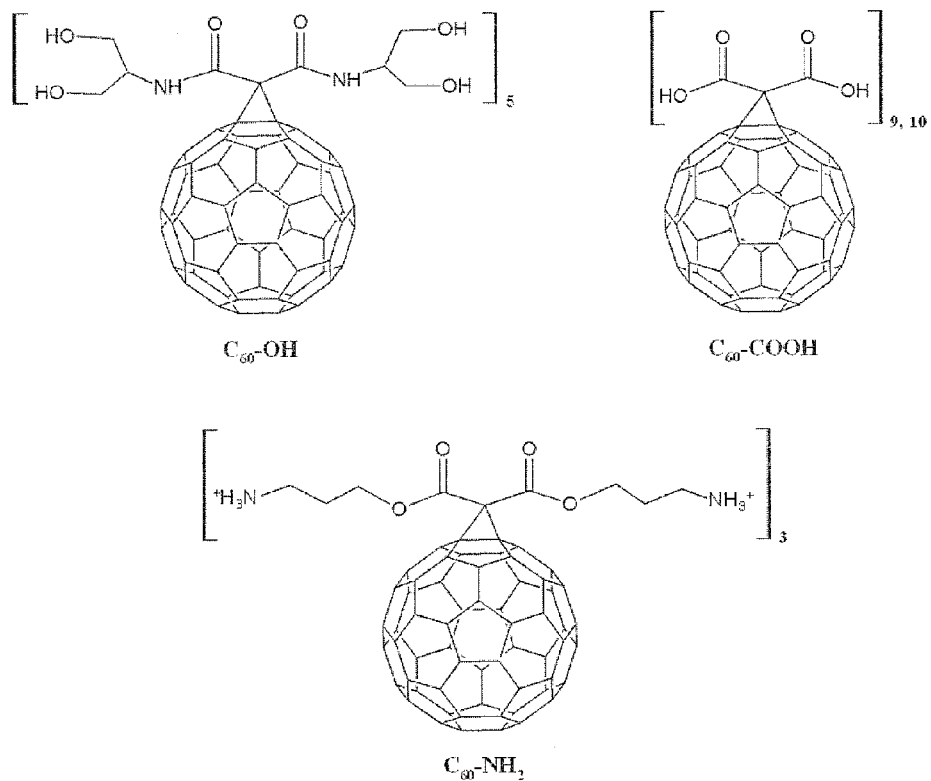
FIG. 2. $C_{60}$ fullerene derivatives used in this study. The fullerene-COOH-derivative carries negative charges in solution, the fullerene-NH$_3^+$-derivative is positively charged. The $C_{60}$-serinol (—OH) is neutral.

In one embodiment, the present method shows that microorganisms can be a good candidate to remediate toxic carbon-based compounds, such as fullerenes shown in FIG. 2, comprising the removal of soluble nanoparticles from water, wastewater or other solutions through the use of bacteria to aggregate and sequester these nanomaterials and precipitate them out of solution. Other carbon nanomaterials and other nanoparticles (e.g., metal, metal oxides, semiconductors) could also be potentially be cleaned by the present bioremediation method.

Potentially any microorganism used in remediation for other substrates are legitimate candidates. In a preferred embodiment, the bacterial organism used is non-pathogenic, such as *Shewanella*. This bacterium can act in aerobic and anaerobic conditions, and certain strains have been shown to be useful for bioremediation of toxic metals such as chromium. See Middleton, S. S., R. B. Latmani, M. R. Mackey, M. H. Ellisman, B. M. Tebo, and C. S. Criddle. 2003. Cometabolism of Cr(VI) by *Shewanella oneidensis* MR-1 produces cell-associated reduced chromium and inhibits growth. Biotechnol. Bioeng. 83:627-637 (which is incorporated by reference). Shewanella strains are a type of Gram-negative, facultative anaerobes that are capable of utilizing many carbon sources (lactate, acetate, pyruvate, and some amino acids) and are capable of reducing a variety of electron acceptors (oxygen, Fe(III), Mn(IV), sulfur, nitrate, and fumarate). There have been extensive studies of *Shewanella* strains, including its versatile respiration and its potential to engage in co-metabolic bioremediation of toxic metals.

Figure 1A:
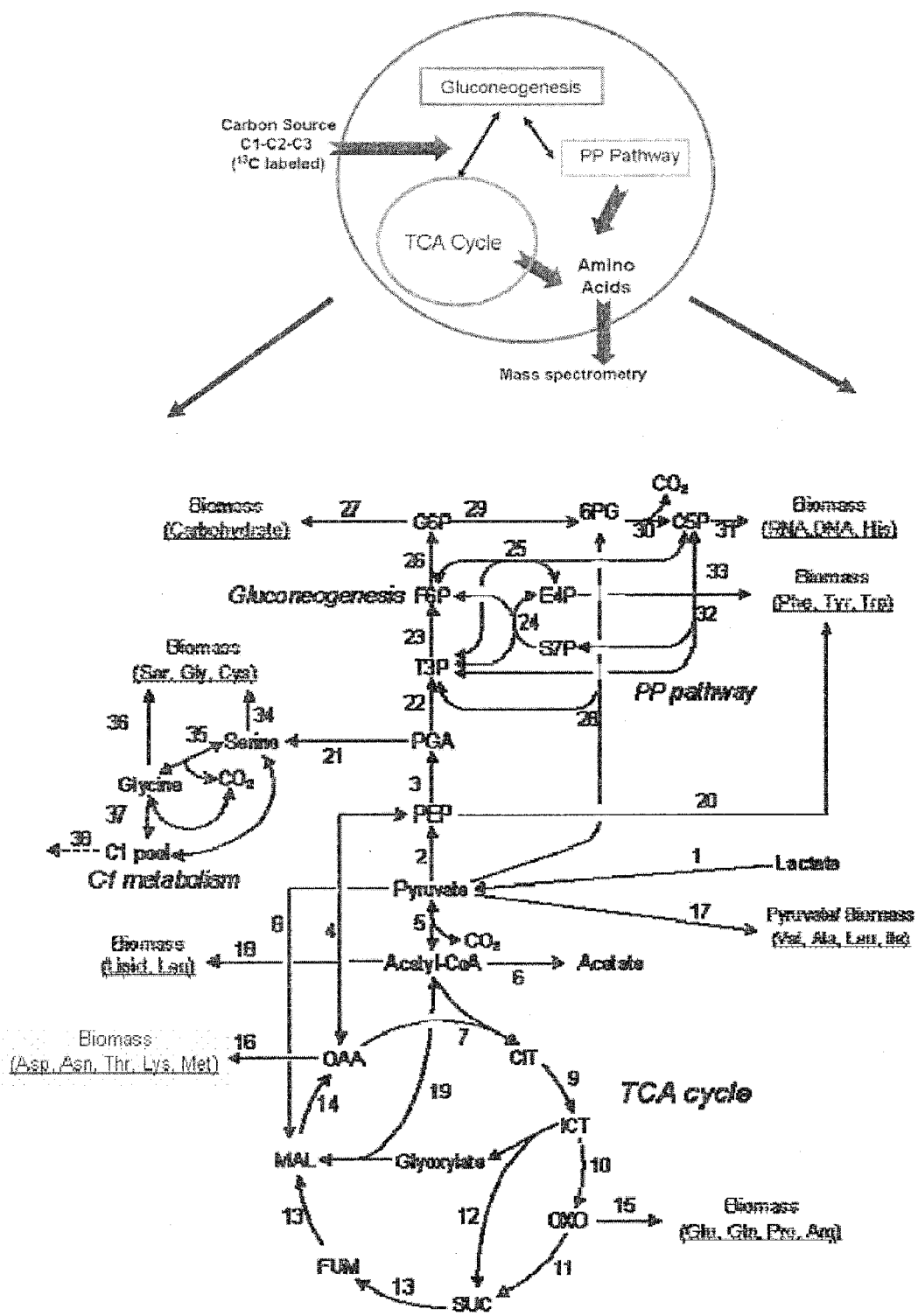
FIG. 1A. Schematics for the isotopic approach of investigating cellular global metabolism via $^{13}$C labeling pattern in amino acids. Labeling patterns of metabolites (often amino acids) were used to evaluate the perturbation of central carbon metabolism in this study. The amino acids used for isotopomer models are in parenthesis. Numbers represent the fluxes used in modeling. Abbreviations: ACoA, acetyl-coenzyme A; CIT, citrate; E4P, erythrose-4-phosphate; C1, 5,10-Me-THF; F6P, fructose-6-phosphate; G6P, glucose-6-phosphate; 6PG, 6-phosphogluconate; ICT, isocitrate; MAL, malate; OAA, oxaloacetate; OXO, 2-oxoglutarate; PEP, phosphoenolpyruvate; PGA, 3-phosphoglycerate; CSP, ribose-5-phosphate (or ribulose-5-phosphate or xylulose-5-phosphate); S7P, sedoheptulose-7-phosphate; SUC, succinate; T3P, triose-3-phosphate; PYR, pyruvate.
Figure 1B:
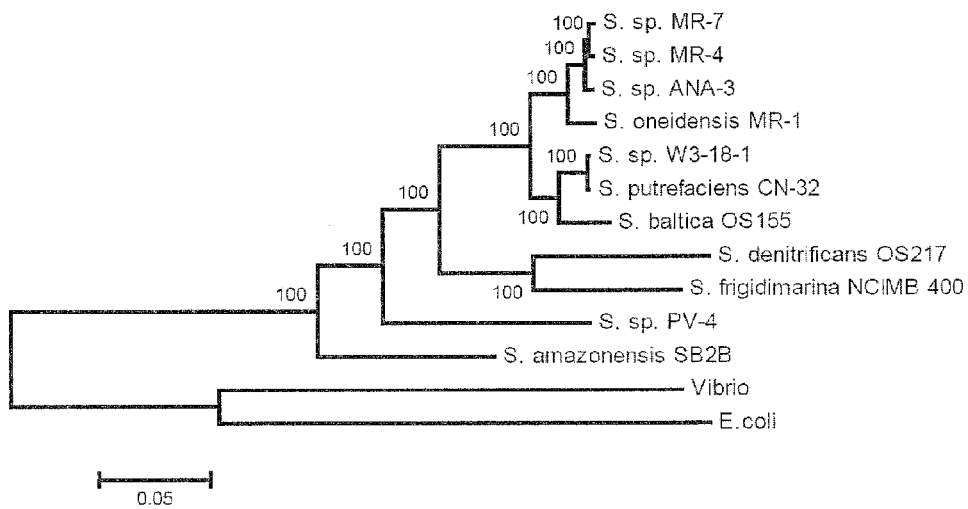
FIG. 1B. Schematic showing the phylogenetic relationship between eleven *Shewanella* strains which can be used in the present invention.

Referring now to FIG. 1B, which shows the phylogenetic relatedness of 11 sequenced *Shewanella* genomes. Eight *Shewanella* strains MR-7, MR-4, ANA-3, MR-1, W3-18-1, CN-32, PV-4 and SB2B can grow in minimal medium (easily grown, no specific nutrients required) and can efficiently precipitate nanoparticles and toxic metals (such as $Cr^{6+}$) as well as reduce nitrate/nitrite (or other toxic compounds) to $NH_4^+$. Those strains can be useful for bioremediation of nanoparticle (or heavy metal) contaminated water.

In one aspect of the method, the cell wall of bacteria is acting as filtering system. Basically, the microbes act as a more efficient filter, with the added capability of self-regeneration. Thus it is contemplated that other organisms with a nano-sized mesh structure in their cell wall can be used in the present method.

The microorganism or bacteria are added to the target solution containing nanoparticles to be remediated. Removal can occur in less than one hour dependent upon the volume of solution, the amount of nanomaterials to be precipitated and the amount of cell culture added. FIG. 8 shows the efficiency of precipitating fullerene-$NH_2$ (40 mg/L) from solution with different concentration biomass (MR-1). It can be expected that nanoparticles in solution will precipitate within 30 minutes after addition of MR-1 cells. It was also found that providing aerobic conditions such as shaking flask cultures allows the cells to grow more quickly and removal of nanomaterials happens at a faster rate.

Over 80 ng/L of nanoparticles were found to kill the cells, thus demonstrating that an increased amount of cell culture should be added to effect remediation. In FIG. 5A, it was found that starting with an O.D. of 0.2 or 0.3, which is about 0.1 g cells/L of solution results in the removal of 20 mg/L of nanoparticles. In another example, it was observed that 100 mg cells can clean about 20~40 mg fullerene compounds. Thus, in a preferred embodiment, relatively high concentrations of cells are used to absorb and remove all nanoparticies from the solution.

Figure 4:
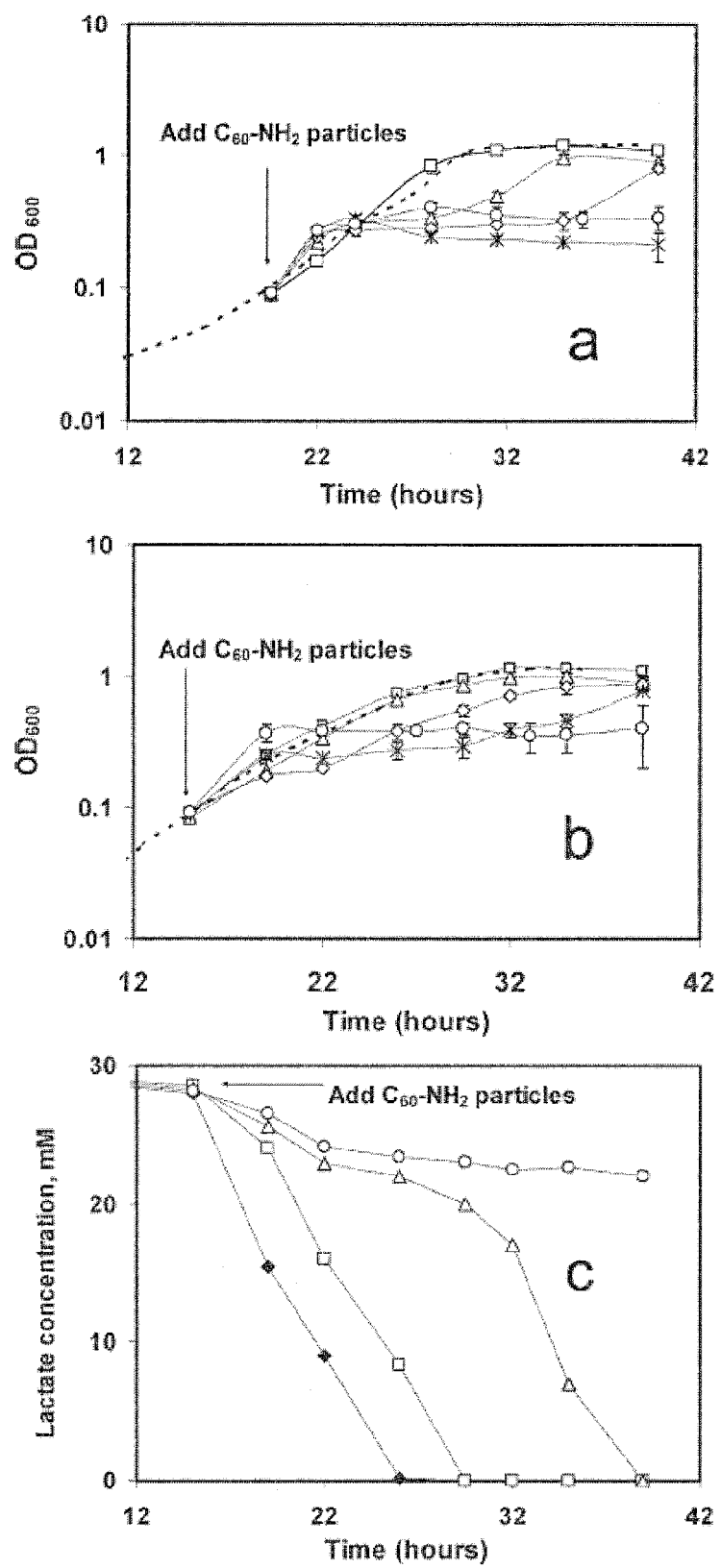
FIG. 4. $C_{60}$—NH$_2$ fullerene (cationic charge) affected *E. coli* W3110 growth (a) and *S. oneidensis* MR-1 growth (b), and *S. oneidensis* MR-1 lactate uptake (c). (a) and (b) - - -, 0 mg/L; □, 1 mg/L; Δ, 10 mg/L; ◇, 20 mg/L; *, 40 mg/L; ○, 80 mg/L. (c) ♦, 0 mg/L; □, 20 mg/L; Δ, 40 mg/L; ○, 80 mg/L.
Figure 5:
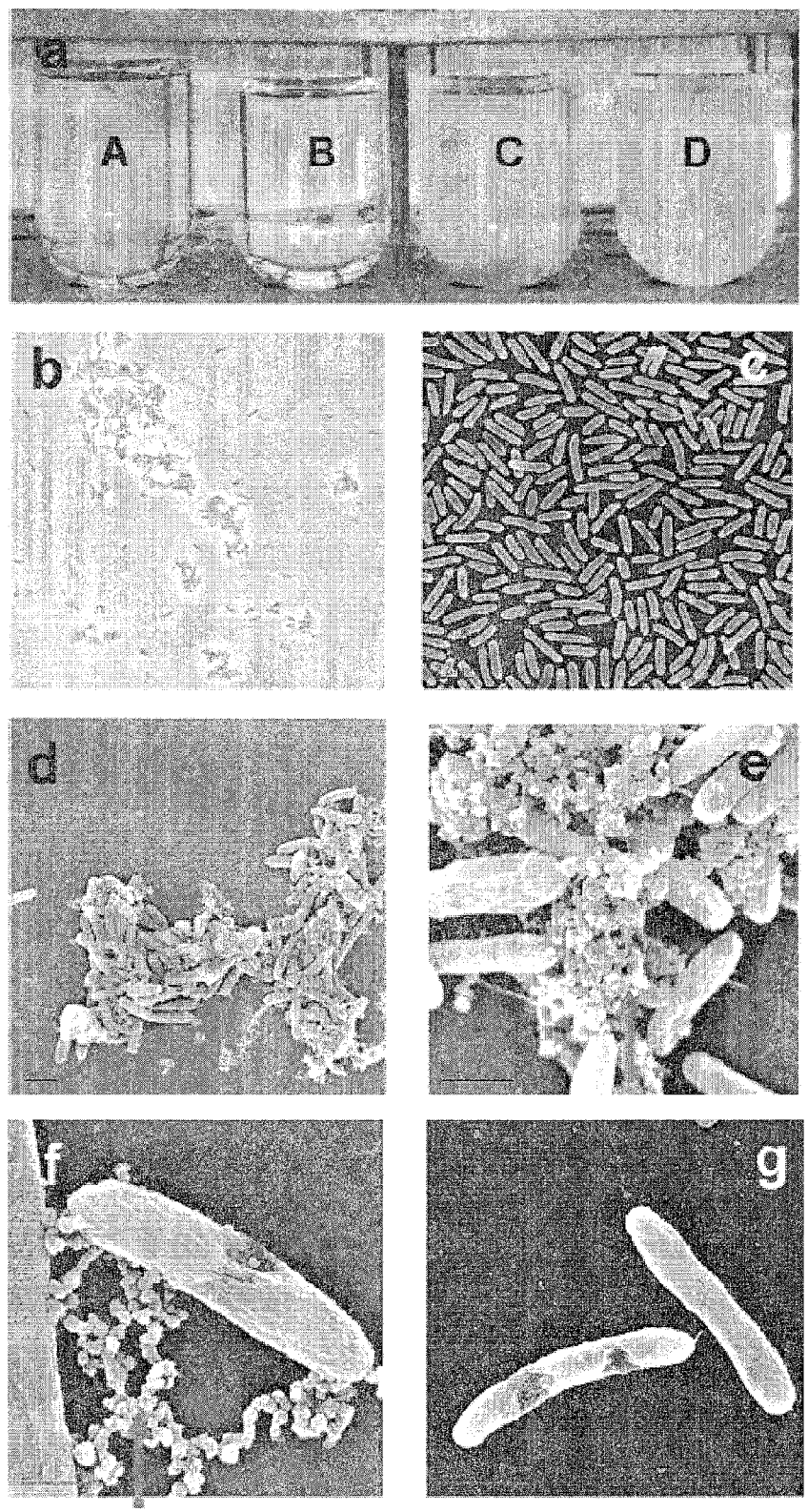
FIG. 5, Images of *S. oneidensis* MR-1 exposed to $C_{60}$—NH$_2$. Micrographs were taken 40 minutes after addition 10 mg/L $C_{60}$—NH$_2$ to log phase cell cultures. Cell samples were fixed for SEM images approximately one hour after exposed to 20 mg/L $C_{60}$—NH$_2$. (a) Precipitation of *S. oneidensis* MR-1 with nanoparticles (Λ: no cells, $C_{60}$—NH$_2$; B: no cells, no nanoparticles; C: *S. oneidensis* MR-1 cells at OD$_{600}$ 0.26, $C_{60}$—NH$_2$ added; D: *S. oneidensis* MR-1 at OD$_{600}$ 0.26, no nanoparticles). (b) Light microscopy showed cell aggregation. (c) SEM of *S. oneidensis* MR-1 (no effect from NPs). (d) SEM of *S. oneidensis* MR-1 aggregation in the presence of $C_{60}$—NH$_2$. (e) SEM of *S. oneidensis* MR-1 in the presence of $C_{60}$—NH$_2$ (green arrow points to nanoparticles). (f) SEM of *S. oneidensis* MR-1 in the presence of $C_{60}$—NH$_2$ aggregation (red arrow points to the damaged part of the cell). (g) SEM of individual *S. oneidensis* MR-1 cells (red arrow points to the damaged part of the cell).

Referring now to FIGS. 4 and 5, the absorbance of light can be used as a measure of the effectiveness of the cells in reduction and aggregation of the suspended nanoparticles. In general, each type of nanoparticle strongly absorbs light at certain wavelengths. The concentration of nanoparticles can be roughly evaluated based on the absorbance at such wavelength in the supernatant. The significant reduced absorbance by suspended nanoparticles in the solution after addition of cells indicates that nanoparticles are removed from the solution.

After allowing the cells sufficient time for aggregation (~30-45 minutes), cells and nanoparticles precipitated in the bottom of container. It may not be necessary to centrifuge or filter the sample, since biomass and nanoparticles precipitate as a solid phase, meaning that the cleaned supernatant out of the container is easily removed, separated or poured from the container.

The effects of four types of fullerene compounds ($C_{60}$, $C_{60}$—OH, $C_{60}$—COOH, $C_{60}$—$NH_2$) were examined on two model microorganisms (*Escherichia coli* W3110 and *Shewanella oneidensis* MR-1). Positively charged $C_{60}$—$NH_2$ at concentrations as low as 10 mg/L inhibited growth and reduced substrate uptake for both microorganisms. Scanning Electron Microscopy (SEM) revealed damage to cellular structures. Neutrally-charged $C_{60}$ and $C_{60}$—OH had mild negative effects on *S. oneidensis* MR-1, whereas the negatively-charged $C_{60}$—COOH did not affect either microorganism's growth. In addition, although $C_{60}$—$NH_2$ compounds caused mechanical stress on the cell wall or membrane, both *S. oneidensis* MR-1 and *E. coli* W3110 can efficiently alleviate such stress by cell aggregation and precipitation of the toxic nanoparticles.

Thus the invention contemplates the present method being used in waste water treatment, whereby the microorganism or bacteria are used to decontaminate wastewater or other solutions contaminated with nanomaterials. For example, in FIG. 7, microorganism or bacteria can be adapted for a bioreactor that is grown in suspension.

In one aspect, the method relies on the bacterial cell wall acting as a mesh or filter that is charged that attracts oppositely or neutral nanoparticles. Thus it is contemplated that to improve the method, bacteria can be engineered to have positively or negatively or hydrophobic cell walls to increase the aggregation and remediation ability of the bacteria. Bacterial cell walls can be modified with carbohydrates, proteins, lipids, and other types of biomolecules. Genes that controls the pore size, charge density, functional group on the cell wall mesh can be altered and modified to generate more efficient cleaning microbe. A screening system based on the absorption efficiency of the microbe can be used as the phenotypical index, and gene expression microarray of the particular microbe can be used to sort out the genes that might be responsible for the enhanced phenotypical properties (absorption, recovering, resistance to nanoparticle-induced damage, aggregation and precipitation). The gene expression of these genes can be altered by mutagenesis of the bacteria and be elevated to allow a more efficient phenotype to emerge from the secondary screening.

In the examples, the absorption of nanoparticles by the cell surface of *Shewanella* are likely due to fullerene's positive electron charges. In another embodiment, *Shewanella* can be engineered to improve its bioremediation performance by over-expression of its nanowire structure. The nanowire structure was observed in Gorby et al., Electrically conductive bacterial nanowires produced by *Shewanella oneidensis* strain MR-1 and other microorganisms. Proc Natl Acad Sci USA. 2006 Jul. 25; 103(30):11358-63, hereby incorporated by reference. The surface of *Shewanella* cell walls displays nano-scaled wires which may present a unique way for efficient electron transfer and energy distribution. Such nanowire structures increase the surface of MR-1 and could efficiently interact with nanoparticles including some nano-scaled metal oxides (e.g., $MnO_2$ and $Fe_3O_4$). Thus, MR-1 is a very good candidate for capturing positive charged toxic compounds. Moreover, our unpublished data showed that Shewanella strain type MR-4 and MR-7 have higher ability against nanotoxicity than MR-1 strain (FIG. 1b). Those strains (or mix) can be even better candidates for the bioremediation purpose.

In another embodiment, a method is provided of isotopomer analysis for indexing the toxicity of carbon-based nanomaterials at the metabolism level. As used herein, by the term, "isotopomer," it is meant, an isomer having the same number of each isotopic atom but differing in their positions. For example, $CH_3CHDCH_3$ and $CH_3CH_2CH_2D$ are a pair of constitutional isotopomers. In the tracer experiments, the carbon istopomer distribution in the metabolites is determined by metabolic fluxes (FIG. 1a). Metabolic flux distribution is a map of the rates of metabolic reactions in the cell. When a carbon substrate (such as glucose) is labeled with a certain pattern of non-radioactive $^{13}C$, the resulting labeling pattern of cellular metabolites (e.g., amino acids, lactate, pyruvate, etc) permits the accurate determination of the metabolic reaction rates (fluxes) through all related pathways. By knowing the isotopic patterns of only 20~30 key metabolites, people can derive the relative rates for enzymatic reactions in the central metabolic network (comprising hundreds of enzymatic reactions).

There are various high throughput methods to quickly identify all the reactions occurring in a cell ("the metabolome"). Others use microarray technology, however the present flux analysis relies on the use of labeling of $^{13}C$ substrate which distributes throughout the metabolome and uses mass spectrometry and $^{13}C$ nuclear magnetic resonance (NMR) to observe key metabolites produced in a cell (e.g., $^{13}C$ labeled amino acids and metabolites) thereby allowing the determination of which metabolic pathways are activated or inactivated and which enzyme reactions are occurring in response to a genetic perturbation or environmental stress. Using isotopomer modeling, accurate metabolic flux values can be obtained.

The present method describes the use of a high throughput isotopomer analysis for nanotoxicity effect on cell metabolism. Briefly the present method comprises the steps of (1) Design the experiment, (2) grow the cell culture, (3) provide non-radioactively labeled medium, (4) measure the isotopomer levels, (5) determine which pathway has been changed and how much the reaction rate has changed by directly comparing the isotopomer changes in proteinogenic amino acids between two different experimental conditions (or two different strains). Two core techniques are used to achieve this goal: 1) precise measurements of the labeling pattern of global metabolites using high-resolution and highly sensitive mass spectrometers (such as GC-MS, ESI-TOF or FT-ICR), and 2) comparison of large isotopomer data sets (i.e., mass spectrometry measurements) from the studied culture condition with the standard control experiment in light of complete metabolic pathway map (including thousands of cellular enzymes), the significant change of isotopic labeling in certain metabolites indicates the perturbation of their enzymatic reactions. The method can be used to mechanistically study the cellular and biomolecular machineries affected by nanomaterials, to determine the effect of nanoparticles on central carbon and energy metabolism, and the effect of perturbation of metabolic flux distributions of cells treated with carbon-based nanomaterials and compounds (FIGS. 1a and b).

In previous research, isotopomer based flux analysis in central metabolism has been used to improve drug production in industrial microorganisms, and for the identification of human pathways which can be critical, for example, for cancer cells. See Stephanopoulos, G.; Aristidou, A.; Nielsen, J., *Metabolic Engineering Principles and Methodologies*. Academic Press: San Diego, 1998; p 75, 120-130; Szyperski, T. *Quarterly Reviews of Biophysics* 1998, 31, (1), 41-88; and Tang, Y.; Hwang, J.; Wemmer, D.; Keasling, J. *Applied and Environmental Microbiology*, February 2007, 73, 3, 718-729 (which are incorporated by reference). However, $^{13}C$ metabolic flux analysis in those published studies is mainly applied to limited central metabolic pathway and the measurement of isotopomer is based on the NMR or GC-MS (not sensitive to low abundant metabolites), which only can describe the simplified metabolic network (<100 reactions). Furthermore, it requires programming algorithms (such as Monte Carlo or simulated annealing optimization routines) to calculate the flux distribution. On the contrary, our isotopomer analysis focuses on comparison of change of isotopomer data between culture conditions to identify the relative perturbation of central metabolisms (we do not need to calculate the flux!), i.e., change of the isotopomer labeling in certain metabolite meaning the reactions related to this metabolites are likely changed. Based on the labeling information from as many as possible metabolites under different culture conditions, this type of isotopomer analysis further enlarges and elaborates the picture of the complete metabolic network. Recently, mass spectrometry-based methods of high-resolution/sensitivity, such as LC-MS and FT-ICR, are becoming increasingly routine in academia and industry, and they can detect very low amounts of metabolites and nearly complete labeling patterns. The isotopic technique thus has a broader and more powerful application to provide detailed information on the regulation of enzymatic activities under environmental stress or genetic mutations through entire metabolism from the isotopomer data in all available metabolites. Potentially, the isotopic labeling is a high throughput approach complementary to microarray study (while using isotopic abundance in metabolites instead of gene expression level) to figure out the change of in vivo enzymatic reaction activities. Thus, the method can be used to probe global enzymatic metabolism in cells and track its perturbations, e.g., changes in gene expression and protein function when cells are exposed to certain environmental and genetic stresses. The ultimate outcome of gene regulation encompasses activity alteration of various cellular enzymes in a network, which is responsible for the overall changes in cellular metabolism and energy production, so this method truly reflects the status and function of cells' metabolism (comprising hundreds of enzymatic reactions) under various conditions.

In one embodiment, isotopomer analysis is used to conduct nanotoxicity studies such as those carried out in Example 2. The effect of fullerene compounds on global metabolism was investigated using [3-$^{13}C$]L-lactate isotopic labeling, which tracks perturbations to metabolic reaction rates in bacteria by examining the change in the isotopic labeling pattern in the resulting metabolites (often amino acids). The $^{13}C$ isotopomer analysis from all fullerene-exposed cultures revealed no significant differences in isotopomer distributions from unstressed cells. This result indicates that microbial central metabolism is robust to environmental stress inflicted by fullerene nanoparticles. The results presented here show that fullerenes may cause more membrane stress than perturbation to energy metabolism.

More detailed and specific isotopomer analysis for measuring nanotoxicity can be implemented. For example, one can use the above analysis to determine which pathway in the chosen strain is affected by a specific type, size, or shape nanoparticle. Furthermore, one can also use the analysis to determine which types of microorganisms provide the best remediation results, and how the perturbation affects each organism.

The present method also enables drug target identification for many diseases. For example, pathogens normally take advantage of regulating specific metabolic pathways to benefit their survival inside hosts. Studying the pathogen metabolic networks may reveal specific pathways important for maintaining their growth or altering host defense mechanism. Gene products (i.e. metabolic enzymes) involved in unique and highly exploited pathways could be potential drug targets to inhibit pathogen replication and survival, while not affecting human metabolism or benign microorganisms living in human guts.

In one embodiment, the method is used to provide unique metabolic profiles correlated with disease states for diagnostics. The isotopic labeling technique may also detect the subtle changes in central metabolism of cells under different disease states. For example, breast cancer cells have higher fluxes through lactate and glutamate production pathways. In vivo (sampling directly from human serum) or in vitro (sampling from human-derived cells cultured in labs) monitoring isotopic labeling patterns of key metabolites produced by tumor cells vs. normal cells could help determine the presence and severity of this disease.

In another embodiment, the method is used in microbial fermentation industry and bioremediation. Isotopomer analysis sheds new insights in understanding metabolism of microorganisms, and identifying the bottleneck pathway(s) induced by genetic engineering. Many synthetic biology applications, such as bio-fuel generation, metal ion remediation and synthesis of medical precursors, are limited in their practicality due to high toxicity on bacteria when new pathways are introduced inside cells. $^{13}C$ labeling experiments can provide critical information on cellular metabolism, which helps the optimization of genetic design to relieve toxic cellular stress.

And in another embodiment, validation of gene function involved in central metabolism. Every year, billions of dollars are spent on sequencing genomes of microorganisms and mammalians. Although the expressed genes may reflect the potential status of a cell, the genuine activities and functions of a cell can not be elucidated without knowing all kinds of post-transcriptional regulation, mostly on proteins and metabolites. Isotopomer analysis allows us to study or validate the function of genes by directly revealing the end effect of their regulation.

Example 1

Materials & Methods

The effects of four types of fullerene compounds ($C_{60}$, $C_{60}$—OH, $C_{60}$—COOH, $C_{60}$—NH$_2$) were examined on two model microorganisms (*Escherichia coli* W3110 and *Shewanella oneidensis* MR-1). Neutrally-charged $C_{60}$ and $C_{60}$—OH had mild negative effects on *S. oneidensis* MR-1, whereas the negatively-charged $C_{60}$—COOH did not affect either microorganism's growth. Although $C_{60}$—NH$_2$ compounds caused mechanical stress on the cell wall or membrane, both *S. oneidensis* MR-1 and *E. coli* W3110 can efficiently alleviate such stress by cell aggregation and precipitation of the toxic nanoparticles. The effect of nanomaterial compounds on global metabolism can be investigated using [3-$^{13}C$] isotopic labeling, which tracks perturbations to metabolic reaction rates in organisms by examining the change in the isotopic labeling pattern in the resulting metabolites (often amino acids). The $^{13}C$ isotopomer analysis from all fullerene-exposed cultures revealed no significant differences in isotopomer distributions from unstressed cells. This result indicates that microbial central metabolism is robust to environmental stress inflicted by fullerene nanoparticles. Based on comparing metabolites' isotopomer data from the studied experiments with standard control, this method are also useful to analyze metabolic perturbation under different environmental conditions or genetic mutations.

Nanoparticles preparation. Sublimed C60 fullerene (purity 99.95%+) was purchased from MER. The carbon MWCNOs used in this study were produced using a modified direct-current electric-arc discharge method, also described in Ding, L.; Stilwell, J.; Zhang, T.; Elboudwarej, O.; Jiang, H.; Selegue, J. P.; Cooke, P. A.; Gray, J. W.; Chen, F. F. *Nano Letters* 2005, 5, (12), 2448-2464, and ano, N.; Wang, H.; Chhowalla, M.; Alexandrou, I.; Amaratunga, G. A. J. *Nature* (*London*) 2001, 414, (29 Nov. 2001), 506-507, both hereby incorporated by reference. The multi-adduct $C_{60}$ serinol ($C_{60}$—OH), carboxylic acid ($C_{60}$—COOH) and amine ($C_{60}$—NH$_2$) derivatives were synthesized using Bingel Chemistry, as described in Bingel, C. *Chemische Berichte-Recueil* 1993, 126, (8), 1957-1959, hereby incorporated by reference.

In brief, $C_{60}$ derivatives were prepared by dissolving 50 mg (0.069 mmol) of $C_{60}$ in 250 mL anhydrous toluene. To this solution, the malonate derivative, CBr$_4$ and DBU were added sequentially. The solution was stirred at room temperature overnight to help ensure the desired degree of functionalization. Toluene was removed under reduced pressure to give the crude products, which were purified by column chromatography. After solvent removal, the purified solids were dried overnight. This gave the desired $C_{60}$ derivatives. MALDI-TOF MS was used to verify the products. The protecting groups of the $C_{60}$ derivatives were then removed using established deprotection procedures to give the water-soluble fullerene compounds (FIG. 2).

Tracer Experiments. *Shewanella oneidensis* MR-1 and *Escherichia coli* W3110 were cultured in minimal medium (described in Tang, Y. J. J.; Laidlaw, D.; Gani, K.; Keasling, J. D. *Biotechnology and Bioengineering* 2006, 95, (1), 176-184) and hereby incorporated by reference). The medium was supplied with 30 mM (98% [3-$^{13}C$]L-lactate) (Cambridge Isotope, USA) as the sole carbon source to support cell growth. The inoculum was prepared in LB medium, which was grown overnight. This culture was inoculated into the minimal medium with a 0.09% inoculation volume. Both *S. oneidensis* and *E. coli* were cultured in shake flasks at 30° C. (at 200 rpm in dark). The fullerene compounds ($C_{60}$, $C_{60}$—OH, $C_{60}$—COOH and C60-NH$_2$) were added to the medium to different final concentrations (from 1 mg/L to 80 mg/L) before the exponential phase (OD$_{600}$=0.09~0.10). The culture's optical density at a wavelength of 600 nm (OD$_{600}$) was measured in a spectrophotometer (DU®640, Beckman Instruments, Palo Alto, Calif.) every 2-3 hours. The carbon source (lactate) concentrations at each time point were determined using an enzyme test kit (r-Biopharm Inc., Darmstadt, Germany).

Isotopomer analysis. Isotopomer analysis was performed as described previously Tang, Y. J.; Meadows, A.; Kirby, J.; Keasling, J. D. *Journal of Bacteriology* 2007, 189(3):894-901; and Tang, Y. J.; Pingitore, F.; Mukhopadhyay, A.; Phan, R.; Hazen, T. C.; Keasling, J. D. *Journal of Bacteriology* 2007, 189(3):940-9; both incorporated by reference. Briefly, 10 mL of culture in the exponential phase (OD$_{600}$=0.6~0.8) was harvested and centrifuged at 10,000×g. The cell pellets were suspend in 1 mL of sterile nanopure water and sonicated for 3 min with a 3 sec. on/1 sec. off cycle. The protein from the resulting lysate was precipitated using trichloroacetic acid. The protein pellet was washed with cold acetone two times; then hydrolyzed in 6 M HCl at 100° C. for 24 hours. GC-MS samples were prepared in 100 μL of tetrahydrofuran (THF) and 100 μL of N-(tert-butyldimethylsilyl)-N-methyl-trifluoroacetamide (Sigma-Aldrich, USA). All samples were derivatized in a water bath at 65-80° C. for 1 hour, producing tert-butyldimethylsilyl (TBDMS) derivatives. One μL of the derivatized sample was injected into GC-MS: a gas chromatograph (Agilent, model HP6890) equipped with a DB5-MS column (J&W Scientific, Falsom Calif.) and analyzed using a mass spectrometer (Agilent, model 5973, Wilmington, Del.). The GC operation conditions are as follows: the GC column was held at 150° C. for 2 minutes, heated at 3° C. per minute to 280° C., heated at 20° C. per minute to 300° C., and held for 5 minutes at that temperature. Unfragmented molecules, [M-57]$^+$ for all amino acids were clearly observed by MS in this study. M is the total molecular mass of the derivatized hydrolysate component, and 57 indicates the loss of 57 mass units, e.g. a tert-butyl group. The natural abundance of isotopes, including $^{13}$C (1.13%), $^{18}$O (0.20%), $^{29}$Si (4.70%) and $^{30}$Si (3.09%) (Si occurs in amino acids derivatized for gas chromatography separation), change the mass isotopomer spectrum and were corrected using a published algorithm to get final GC-MS data in Wahl, S. A.; Danner, M.; Wiechert, W. *Biotechnol Bioeng* 2004, 85, (3), 259-68), hereby incorporated by reference. Fourteen amino acids were used in this study (tryptophan, proline, isoleucine, arginine, glutamine and asparagines mass peaks were not used due to their degradation during hydrolysis or due to the overlay of their main MS peaks with other MS peaks).

Light microscopy and scanning electron microscopy (SEM) pictures. *S. oneidensis* and *E. coli* cultures in the late exponential growth phase (OD=0.7~0.9) exposed to nanoparticles were collected and directly observed under light microscopy (LEICA DM4000B). Meanwhile, SEM imaging was carried out as follows: Samples were fixed with 2% glutaradehyde in 0.1 M sodium cacodylate buffer at pH 7.2 for an hour. Fixed samples were rinsed in buffer and then immersed in secondary fixative (1% aqueous osmium tetroxide in buffer) for 30 min. Dehydration of sample was carried out through increasing concentrations of ethanol, further dried in critical point drier and coated with 1.2 nm of Iradium in a MED-020 sputter coater. Images were collected with a Hitachi S-5000 field emission scanning electron microscope, operated at 10 kV.

Example 2

Using Bacteria for Bioremediation of Nanomaterials

The effects of four types of fullerene compounds ($C_{60}$, $C_{60}$—OH, $C_{60}$—COOH, $C_{60}$—NH$_2$) were examined on two model microorganisms (*Escherichia coli* W3110 and *Shewanella oneidensis* MR-1). Neutrally-charged $C_{60}$ and $C_{60}$—OH had mild negative effects on *S. oneidensis* MR-1, whereas the negatively-charged $C_{60}$—COOH did not affect either microorganism's growth. Although $C_{60}$—NH$_2$ compounds caused mechanical stress on the cell wall or membrane, both *S. oneidensis* MR-1 and *E. coli* W3110 can efficiently alleviate such stress by cell aggregation and precipitation of the toxic nanoparticles. The effect of nanomaterial compounds on global metabolism can be investigated using [3-$^{13}$C] isotopic labeling, which tracks perturbations to metabolic reaction rates in organisms by examining the change in the isotopic labeling pattern in the resulting metabolites (often amino acids). The $^{13}$C isotopomer analysis from all fullerene-exposed cultures revealed no significant differences in isotopomer distributions from unstressed cells. This result indicates that microbial central metabolism is robust to environmental stress inflicted by fullerene nanoparticles. Based on comparing metabolites' isotopomer data from the studied experiments with standard control, this method are also useful to analyze metabolic perturbation under different environmental conditions or genetic mutations.

Figure 3:
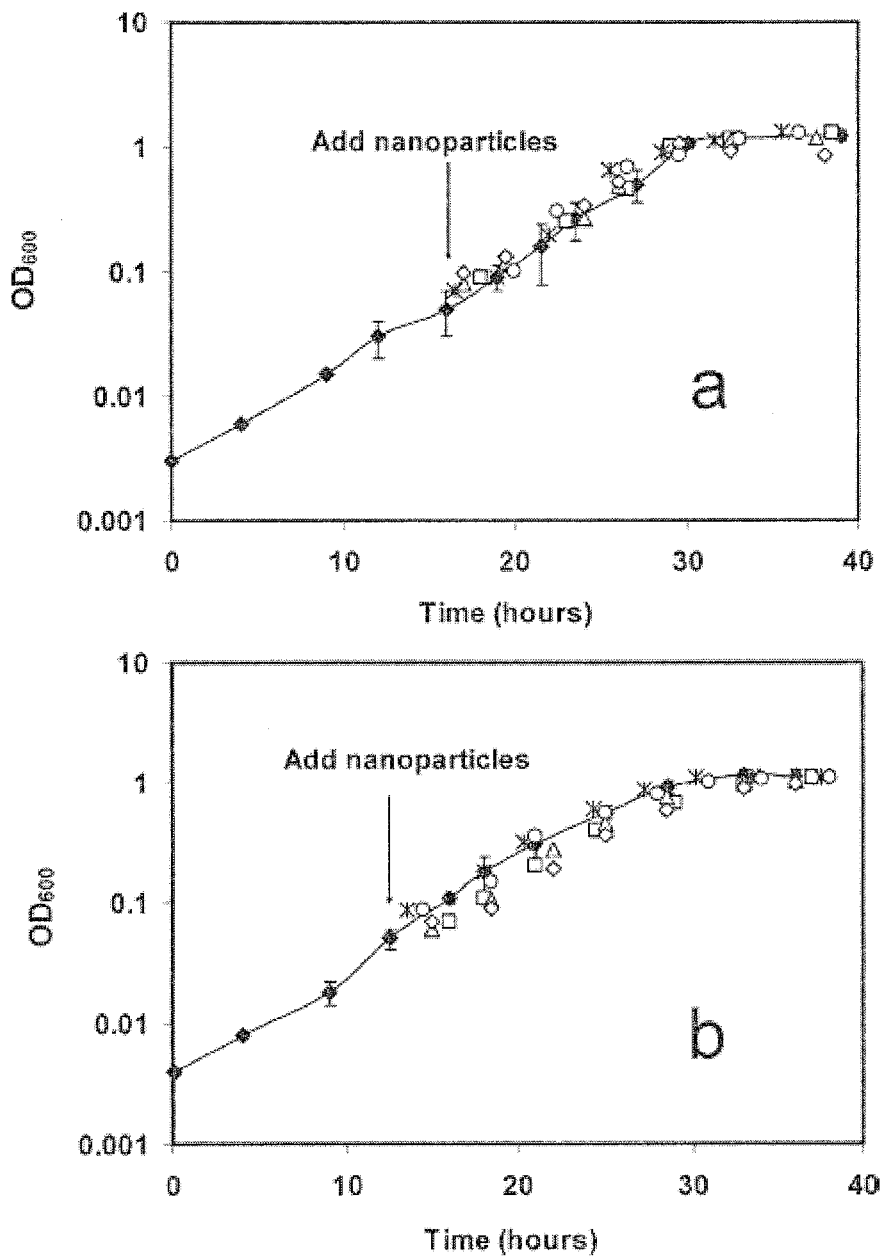
FIG. 3. The effect of $C_{60}$, $C_{60}$—OH, $C_{60}$—COOH fullerene compounds (neutral or anionic charge) on *E. coli* W3110 (a) and *S. oneidensis* MR-1 (b) growth. ♦, control, 0 mg/L; □, $C_{60}$, 20 mg/L; Δ, $C_{60}$—OH, 20 mg/L; ◇, $C_{60}$—OH, 80 mg/L; *, $C_{60}$—COOH, 20 mg/L; ○, $C_{60}$—COOH, 80 mg/L.

We used minimal medium containing [3-$^{13}$C]L-lactate to grow both organisms and test the impact of fullerenes (concentrations range from 0~80 mg/l) on their growth. Since $C_{60}$ is not soluble in water and cannot be uniformly suspended in the culture solution, we only applied concentrations less than 20 mg/L in the studies of non-derivatized $C_{60}$. The results indicated that the addition of anionic fullerene ($C_{60}$—COOH) and neutrally charged fullerene (C60 and $C_{60}$—OH) did not significantly inhibit (concentrations up to 80 mg/L) *E. coli* and *S. oneidensis* growth (FIG. 3*a-b*). This evidence is consistent with previous conclusions that fullerene and anionic fullerene compounds do not affect Gram-negative bacteria. At high concentrations (>40 mg/L), $C_{60}$—OH only mildly slowed *S. oneidensis* growth (not for *E. coli*) by reducing the growth rate 10-20%. On the other hand, the positively charged $C_{60}$—NH$_2$ strongly inhibited the growth of both microorganisms at concentrations as low as 10 mg/L. The cell growth was completely inhibited at high concentration (80 mg/L). It is interesting that at various $C_{60}$ concentrations (20 mg/L and 40 mg/L), *E. coli* and *S. oneidensis* growth slowed after addition of nanoparticles, then resumed their normal growth rate after certain period of lag (several hours) (FIG. 4*a-b*). For the slow growth under $C_{60}$—NH$_2$ stress, slower lactate consumption rates were also observed (FIG. 4*c*).

In order to further understand cell response to nanoparticle stress, changes in bacterial morphology were examined with light microscopy and SEM. Both *E. coli* and *S. oneidensis* aggregated after addition of $C_{60}$—NH$_2$; no aggregation was observed in the presence of other fullerene compounds. For example, uniformly distributed *S. oneidensis* MR-1 started to aggregate right after addition of $C_{60}$—NH$_2$ at concentration as low as 10 mg/L (FIGS. 5*a* and *b*). It has been reported previously that aggregation of *S. oneidensis* MR-1 was associated with oxidative stress and aggregation could be a protection mechanism. Moreover, for the cells that aggregated upon addition of nanoparticles, some cells showed substantial damage (FIG. 5*c-g*). The formation of cell debris and the large amount of cell/nanoparticle aggregates resulted in a sudden increase in the turbidity of the culture (measured by OD$_{600}$), right after addition of a high concentration of $C_{60}$—NH$_2$ (FIGS. 4*a, b*). This evidence supports previous observation that fullerene compounds (carboxyl-fullerene) intercalate into the cell wall and cell membrane in some Gram positive bacteria. The fullerene compounds might have caused the destruction of membrane integrity in bacteria. On the other hand, bacteria may produce certain membrane proteins to strengthen its membrane structure in response to nanoparticle stress to reduce its membrane's permeability. We also observed that bacteria (especially *S. oneidensis* MR-1) can efficiently remove soluble $C_{60}$—NH$_2$ at high concentration by adsorbing and precipitating them (FIGS. 5*a, e*). After that, a normal growth rate and substrate uptake rate were resumed (FIGS. 4*b, c*). The fact that *S. oneidensis* MR-1 efficiently precipitates and absorbs the nanoparticles makes this microorganism a potential bioremediation candidate for soluble cationic nanoparticle pollution.

Figure 6:
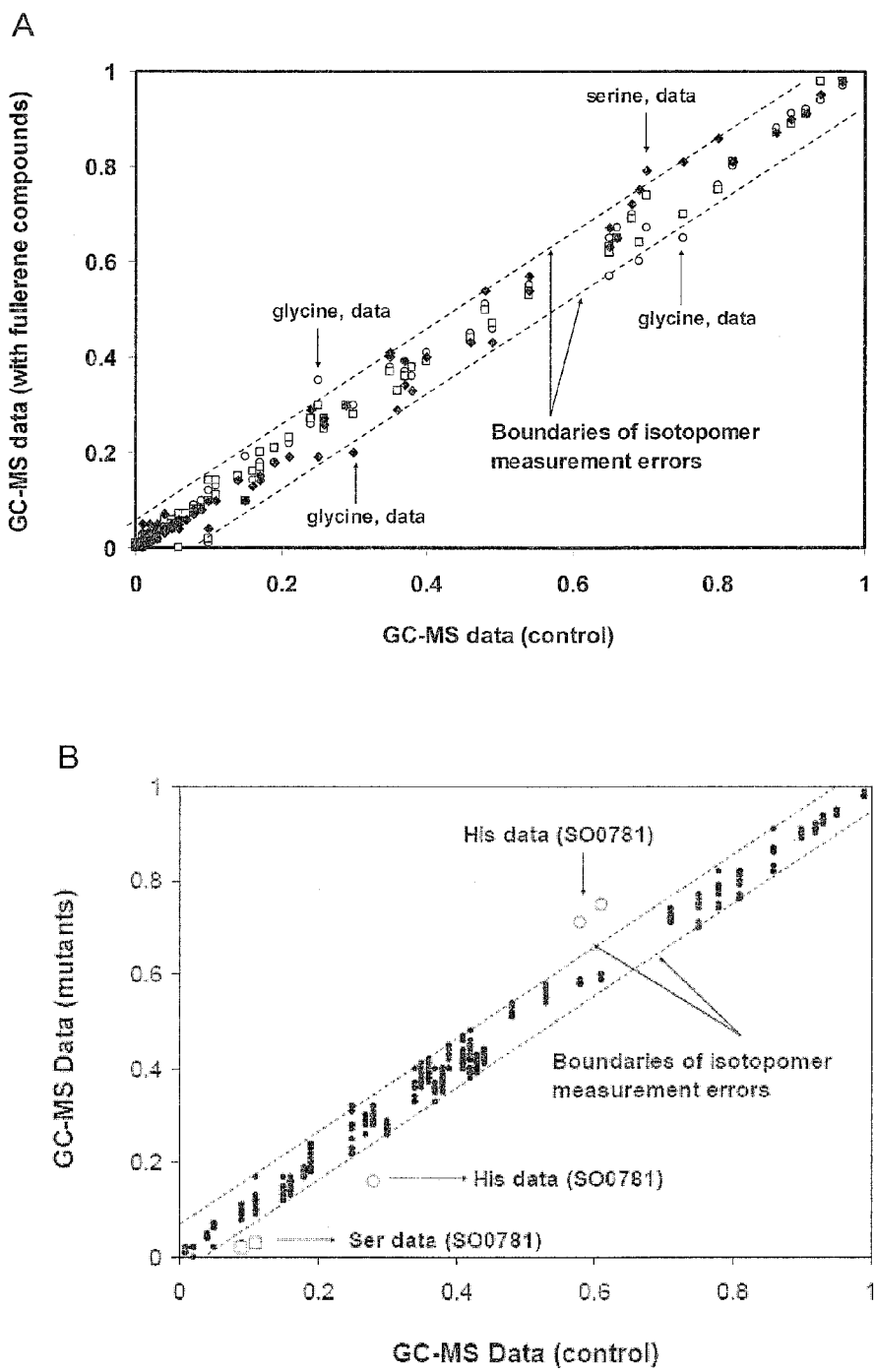

In previous studies with human cell lines, nanoparticles were found to inhibit enzyme activity by interacting with the hydrophobic cavity of certain enzymes and inducing oxidative stress, and thus have been investigated as therapeutic agents against enteric pathogens. These redox-active nanoparticles may interact with a variety of essential enzymes related to energy and biosynthesis pathways, such as cytochrome P450s, cysteine and serine proteases, etc. However, the influence of nanoparticles on microbial central metabolism is poorly understood. To better understand the metabolic fluxes under nanoparticle influence, we administered [3-$^{13}$C] lactate as the sole carbon source to *S. oneidensis* in order to monitor its growth under the effect of the nanoparticles. The fraction of $^{13}$C label in the resulting 14 amino acids was analyzed. These amino acids were synthesized from the precursors in the central metabolic pathways including the TCA cycle, pentose phosphate pathway, and glycolysis. The variance of $^{13}$C-labeled isotopomers for batch cultures was expected to have <10% measurement error, and data for most amino acids in bacterial biomass (both *E. coli* and *S. oneidensis*) cultured in presence of different nanoparticles showed that there were no significant differences in the isotopomer distribution over the measurement noise compared to the control experiments, even for the cultures treated with high concentrations of $C_{60}$—$NH_2$ (FIG. 6a). Only isotopomer data for glycine and serine (related to C1 metabolism) were slightly affected (if at all) by $C_{60}$—$NH_2$ and $C_{60}$—OH nanoparticles. The fact that nanoparticle-stressed cells showed no significant differences in the isotopomer distributions of key metabolites indicates that most enzymes and proteins involved in central carbon metabolism and the amino acid biosynthesis pathway were not seriously perturbed. These observations are not surprising given the robustness of bacterial central metabolism. Such stability of central metabolism against environmental stress is an important characteristic for bacterial survival under hazardous environmental conditions.

Same concept is also applied to screen the Shewanella mutagenesis effect (FIG. 6b). For example, we randomly block genes in *Shewanella oneidensis* MR-1 and get 10 mutants. Based on the isotopomer data from proteinogenic amino acids, we find one of mutants gives the outliers in histidine and serine labeling data, and both amino acids synthesis requires 5,10-Me-THF. Our later sequence on this mutant finds out this mutant is actually bears a deficiency of one of the two 5,10-Me-THF synthesis pathways (glycine→5,10-Me-THF) SO0781 (lack of glycine cleavage system P protein). Therefore, this technique can not only be used for probing nanotoxicity effect on central metabolism, but also detects the effect of genetic changes on cell metabolism.

In addition, we also tried other nanoparticles including gold particles (30 nm) and carbon onion (onion-like fullerenes) for their effect on both *E. coli* and *S. oneidensis* growth; there was no effect on the growth of these bacteria (Table 1). The reported assessments of fullerene toxicity conflict with those in the literature. In general, non-derivatized, anionic and neutral fullerenes have the least impact on bacteria (especially Gram negative bacteria), whereas cationic fullerene compounds have high antimicrobial activity. This can be explained by the negative charges on the bacterial surface that is responsible for the strong adsorption of positively charged nanoparticles, and the enhanced interaction of the nanoparticles with the cell surface. Unlike animal cells, many bacteria are generally more resistant to nanoparticles. This may be due to the robust bacterial cell wall, which might provide extra protection against nanoparticles, and robust central metabolism.

TABLE 1

Nanoparticles effect on the microbes

| References | Nanoparticles | Bacteria types | Conclusions |
| --- | --- | --- | --- |
| This present application | $C_{60}$, $C_{60}$—OH, $C_{60}$—COOH and $C_{60}$—$NH_2$ (0~80 mg/L) | *E. coli* K12 and *Shewanella oneidensis* MR-1 | Only $C_{60}$—$NH_2$ had acute effect. |
| This present application | Gold (30 nm), (0 mg~80 mg/L) Carbon onion, 10 mg/L | *E. coli* K12 and *Shewanella oneidensis* MR-1 | No effect on both bacteria |
| Chiron J P et al., Ann. Pharm. Fr. 2000, 58 (3), 170-175 | Fullerene, ~43 mg/L | 22 collection strains including *E coli*, *B. subtilis*, etc. | No effect |
| Tegos G P et al., Chem Biol. 2005, 12 (10), 1127-1135 | Six functionalized C(60) with hydrophilic or cationic groups (10-100 µM) | Gram-positive bacteria, Gram-negative bacteria, and fungi | In combination with white light, cationic fullerenes were highly active in killing all tested microbes |
| Tsao, N. et al., Antimicrob. Chemother. 2002, 49 (4), 641-649 | The trimalonic acid derivative of fullerene, 50 mg/L | 20 strains, Gram negative or positive, including *E coli* and *Streptococcus pyogenes* | Damage to the cell membrane in Gram-positive, but not Gram-negative, bacteria was observed. |
| Fontner J D et al., Environ. Sci. Technol. 2005, 39 (11), 4307-4316 | Underivatized $C_{60}$ and $C_{60}$—OH (up to 5 mg/L) | *E. coli*, and *B. subtilis* | underivatized $C_{60}$ at relatively low concentrations is inhibitory to prokaryotic microorganisms. $C_{60}$—OH did not affect the growth. |
| Mashino T. el al., Med. Chem. Lett. 2003, 13 (24), 4395-4397 | alkylated C(60)-bis(N,N-dimethylpyrrolidinium iodide) derivatives (up to 100 mg/L) | Gram positive bacteria (*S aureus*, *E. hirae*, *E faecalis*) | The fullerene derivatives inhibited tested bacteria growth effectively. |

This study is one of the first to explore the microbial metabolic perturbation effected by nanoparticles. Although central metabolism in the bacteria studied here does not seem to be strongly influenced by fullerene nanoparticles, the grow inhibition was obvious for the positively charged fullerenes. On the other hand, the SEM morphological results here favor the membrane stress hypothesis. The association of positively charged fullerenes with the negatively charged membranes is more efficient than that of neutral and negatively charged fullerenes. These data support the charge-associated effects. Plausible explanations for the membrane damage are that the fullerenes induce redox damage on the membrane, or the fullerenes mechanically damage the lipid bilayers in the cell membrane. It seems less likely that the energy metabolism perturbation is the major cause for the microbial growth inhibition observed here.

The above compounds, materials, methods and examples are provided to illustrate the invention but not to limit its scope. Other variants of the invention will be readily apparent to one of ordinary skill in the art. All publications, databases, and patents cited herein are hereby incorporated by reference for all purposes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A method for bioremediation of nanomaterials from a liquid mixture, comprising:
    (a) providing a solution containing nanomaterials in suspension;
    (b) adding a *Shewanella* microorganism to said solution;
    (c) allowing the *Shewanella* microorganism to aggregate the nanomaterials and precipitate the nanomaterials; and
    (d) separating the precipitated nanomaterial and the remaining solution;
   wherein the nanomaterials are fullerene particles.

2. The method of claim 1, wherein the ratio of microorganism to fullerene particles is greater than 2.5:1.

3. The method of claim 2, wherein the ratio of microorganism to fullerene particles is greater than 5:1.

4. The method of claim 1, wherein the fullerene particles comprise neutral fullerene compounds, negatively-charged fullerene compounds, positively-charged fullerene compounds, or a mixture thereof.

5. The method of claim 4, wherein the neutral fullerene compound is $C_{60}$ or $C_{60}$—OH.

6. The method of claim 4, wherein the negatively-charged fullerene compound is $C_{60}$—COOH.

7. The method of claim 4, wherein the positively-charged fullerene compound is $C_{60}$—$NH_2$.

8. The method of claim 1, wherein the *Shewanella* microorganism is a *Shewanella oneidensis, Shewanella putrefaciens, Shewanella baltica, Shewanella denitrificans, Shewanella frigidimarina*, or *Shewanella amazonesis*.

9. The method of claim 8, wherein the *Shewanella* microorganism is *Shewanella oneidensis* MR-1.

10. The method of claim 1, wherein the ratio of microorganism to fullerene particles is greater than 12:1.

11. A method for removal of fullerene nanoparticles from a liquid stream, comprising:
    (a) providing a solution containing fullerene nanoparticles in suspension;
    (b) adding a sufficient amount of a *Shewanella* microorganism to said solution;
    (c) allowing the *Shewanella* microorganism to aggregate and precipitate the fullerene nanoparticles; and
    (d) separating the precipitated nanoparticles and the remaining solution;
   wherein the ratio of *Shewanella* to fullerene nanoparticles is greater than 5:1.

12. The method of claim 11, wherein the ratio of *Shewanella* to fullerene nanoparticles is greater than 12:1.

* * * * *